(12) United States Patent
Venables et al.

(10) Patent No.: US 9,936,721 B2
(45) Date of Patent: Apr. 10, 2018

(54) DRINK STABILIZER COMPOSITION AND STABILIZED DRINK COMPOSITIONS

(71) Applicant: FMC Corporation, Philadelphia, PA (US)

(72) Inventors: Aaron Chip Venables, Yardley, PA (US); David Letinski, Hillsborough, NJ (US)

(73) Assignee: DuPont Nutrition USA, Inc., Wilmington, DE (US)

( * ) Notice: Subject to any disclaimer, the term of this patent is extended or adjusted under 35 U.S.C. 154(b) by 0 days.

(21) Appl. No.: 14/836,450

(22) Filed: Aug. 26, 2015

(65) Prior Publication Data

US 2016/0058042 A1   Mar. 3, 2016

Related U.S. Application Data

(60) Provisional application No. 62/071,135, filed on Sep. 15, 2014, provisional application No. 62/042,324, filed on Aug. 27, 2014.

(51) Int. Cl.

| | | |
|---|---|---|
| A23L 1/0528 | (2006.01) | |
| A23L 2/52 | (2006.01) | |
| A23C 9/154 | (2006.01) | |
| A23C 11/10 | (2006.01) | |
| A23L 2/66 | (2006.01) | |
| A23L 29/244 | (2016.01) | |
| A23L 29/269 | (2016.01) | |

(52) U.S. Cl.
CPC ............ *A23L 1/0528* (2013.01); *A23C 9/154* (2013.01); *A23C 11/103* (2013.01); *A23L 2/52* (2013.01); *A23L 2/66* (2013.01); *A23L 29/244* (2016.08); *A23L 29/27* (2016.08); *A23V 2002/00* (2013.01)

(58) Field of Classification Search
None
See application file for complete search history.

(56) References Cited

U.S. PATENT DOCUMENTS

| | | | |
|---|---|---|---|
| 4,369,125 A | 1/1983 | Kragen et al. | |
| 4,582,714 A | 4/1986 | Ford et al. | |
| 4,676,976 A | 6/1987 | Toba et al. | |
| 4,938,983 A | 7/1990 | Peignier et al. | |
| 5,066,508 A | 11/1991 | Schuppiser et al. | |
| 6,180,159 B1 | 1/2001 | Villagran et al. | |
| 6,673,384 B1 * | 1/2004 | Villagran | A23G 1/56 426/575 |
| 7,037,539 B2 | 5/2006 | Westphal et al. | |
| 8,003,152 B1 | 8/2011 | Xiong et al. | |
| 2002/0019447 A1 | 2/2002 | Renn | |
| 2006/0099324 A1 | 5/2006 | Aurio et al. | |
| 2012/0021112 A1 * | 1/2012 | Sworn | A23L 1/0541 426/549 |

FOREIGN PATENT DOCUMENTS

| | | | |
|---|---|---|---|
| CN | 103564277 A | | 2/2014 |
| WO | WO-98-33394 | * | 8/1998 |

OTHER PUBLICATIONS

EPO Supplementary European Search Report for Application No. EP 15836451; Oenhausen, Claudia, Examiner; dated Dec. 1, 2017.

\* cited by examiner

*Primary Examiner* — Celeste A Roney

(57) ABSTRACT

Provided is a composition containing an admixture of xanthan gum and konjac mannan in a specific weight ratio that is useful for making a stable aqueous hydrocolloid. Also provided is a stabilized drink composition containing an admixture of a specific weight ratio of xanthan gum to konjac mannan, protein solids, water and optionally a salt. Also provided is a method for stabilizing aqueous colloid suspensions. Also provided is a method for stabilizing drink compositions.

20 Claims, 1 Drawing Sheet

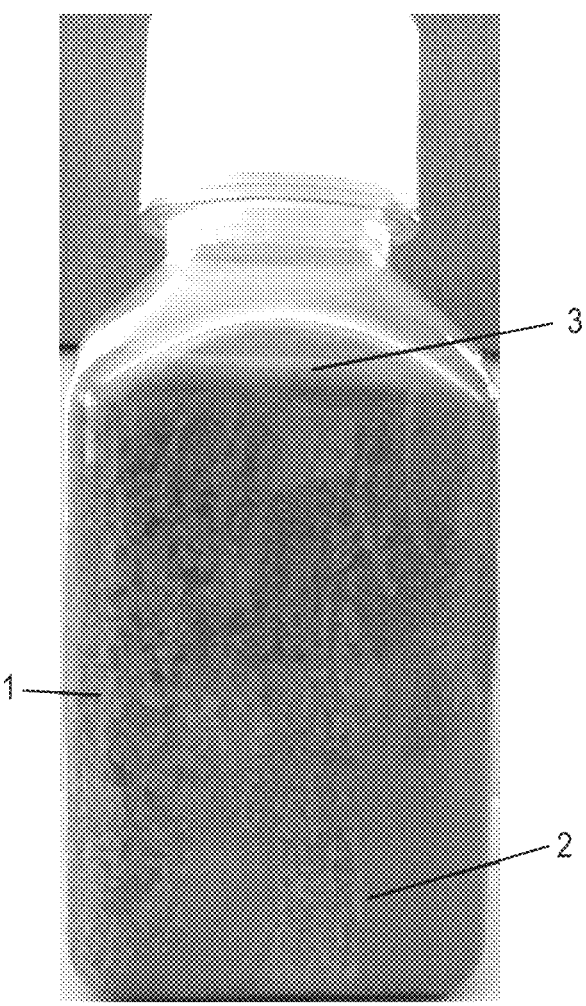

US 9,936,721 B2

DRINK STABILIZER COMPOSITION AND STABILIZED DRINK COMPOSITIONS

FIELD OF THE INVENTION

The invention relates to an improved drink stabilizer composition containing the combination of xanthan gum and konjac mannan. The invention also relates to methods of stabilizing drink compositions using the improved drink stabilizer and drink products comprising the improved drink stabilizer, water-insoluble solids, and water.

BACKGROUND OF THE INVENTION

Stabilization of aqueous suspensions or colloids containing water-insoluble particles is a problem that is encountered in many industries including agriculture, food and beverage, petroleum, and paint industries. Sedimentation and phase separation of aqueous suspensions or colloids containing water-insoluble particles during storage and transportation may require the additional process of re-homogenization at the point of use. Re-homogenization may be costly, difficult to perform, or impractical.

Carrageenan, an extract of red seaweed, is widely recognized as an effective stabilizer and texturizer and its use in the food and beverage industry has been increasing over many years. The stabilizing effects of carrageenan are well known in the art. Carrageenan forms a thixotropic system and when properly utilized can indefinitely stabilize aqueous suspensions or colloids containing water-insoluble particles. However, carrageenan does not possess its full stabilizing functionality unless completely dissolved and does not readily dissolve unless processed using the proper heating, stirring, and cooling procedures. Furthermore in drink applications, carrageenan must be present in a relatively narrow range of concentration in order to stabilize the suspension or colloid. Too much carrageenan results in a gelled, pudding-like solution that is not acceptable for drink applications. Too little and the water-insoluble particles settle to form sediment. Traditionally, beverage-stabilizing grades of carrageenans have been extracted from wild-harvested seaweeds. However, there is a limit to the supply of wild harvested seaweeds. As a result, there is a need for effective alternative stabilizer systems for beverages.

The polysaccharide xanthan gum is a hydrocolloid that is manufactured using a natural fermentation process involving the microorganism *Xanthomonas campestris*. Xanthan gum is commonly used as an additive in the food industry as a hydrophilic colloid to thicken and stabilize emulsions, foams, and suspensions. In processed foods, xanthan gum provides stability and improves or modifies textural qualities, pouring characteristics and cling. Xanthan gum is unique in its rheology in that while it does not form gels, it exhibits pseudo-plastic flow with very high viscosity at low shear rates and low viscosity at high shear rates. In general, the concentration of xanthan gum required for effective stabilization is related to the particle size and density of the water-insoluble particles. In many cases, the concentration required to effectively stabilize the solution may result in unwanted results including excessive viscosity. Therefore, it may not be possible to prevent sedimentation and phase separation while maintaining the desired flow characteristics of drink applications. Finally, even at high concentration, xanthan gum may not be able to eliminate all sedimentation. In the event that sedimentation does occur, the increased viscosity due to the presence of xanthan gum makes re-suspension of sediment particles significantly more difficult.

*Konjac* mannan is a glucomannan extracted from the root of the *Konjac* plant (*Amorphophallal konjac*). *Konjac* mannan has a high capacity for water absorption and can swell to about 200 times its original volume. *Konjac* mannan is unique in that it has the highest viscosity of any known dietary fiber. Due to its high viscosity and capacity for water absorption, *konjac* mannan has been proposed for use in emulsions to increase stability and as a thickening agent. See U.S. Pat. No. 4,582,714. *Konjac* mannan is commercially available in several different manufacturers. *Konjac* mannan has been added to juice drinks in a concentration of approximately 0.01% by weight of the mixture to increase the viscosity of the drink. See U.S. Pat. No. 7,037,539. *Konjac* mannan has also been suggested as an additive for providing a creamy mouth feel to drinks. See U.S. Pat. No. 6,180,159. However, *konjac* mannan solutions are difficult to prepare. Even at low concentration and relatively high temperatures, *konjac* mannan requires rigorous agitation to fully dissolve. Furthermore, the viscosity of *konjac* mannan gels are not shelf stable as the viscosity decreases by a significant amount within 5 to 10 hours at room temperature. See U.S. Pat. No. 8,003,152.

Xanthan gum and glucomannan, such as *konjac* mannan, synergistically interact to form strong, self-supporting, elastic, and thermally reversible gels. Several factors may affect gel strength of a gel resulting from the combination of xanthan gum and glucomannan. For example, gel strength may be enhanced by heating the mixture of xanthan gum and glucomannan above the coil-helix transition of xanthan gum. The ionic strength of the solvent in which xanthan gum and glucomannan are dissolved has an inverse relationship with gel strength. Therefore, increasing the salt concentration or lowering the pH results in weaker gels. The degree of acetyl substitution is also inversely related to gel strength (i.e. decreasing acetylation increases gel strength). See U.S. Patent Application Publication US 2012/0021112 A1. However, the previously described gels resulting from xanthan gum and glucomannan do not have the flow characteristics required for use in drink applications. Xanthan gum is also known to synergistically interact with galactomannans to provide greater viscosity than provided by the use of either element alone. Xanthan gum and other viscous soluble fibers also interact with certain proteins wherein the protein decreases the viscosity of the soluble fiber. For example, proteins include wheat protein, egg protein, collagen protein, whey protein, casein protein, gluten, pea protein, soy protein, silk protein, and combinations thereof, lower the viscosity of *konjac* mannan, xanthan gum, guar gum, beta glucan, and pectin compositions. See U.S. Patent Application Publication US 2006/0099324.

To conclude, there is still a need for a drink stabilizing composition that minimizes phase separation and sedimentation while also providing creamy mouth feel and smooth flow characteristics desired in drink applications.

OBJECT OF THE INVENTION

It is an object of the embodiments of the invention to provide improved drink stabilizing compositions containing the combination of xanthan gum and *konjac* mannan, methods of stabilizing drink compositions using the improved drink stabilizer, and drink compositions containing the improved drink stabilizer.

SUMMARY OF THE INVENTION

The present invention provides a composition for making a stable hydrocolloid including an admixture of *konjac* mannan and xanthan gum wherein the weight ratio of *konjac* mannan and xanthan gum is about 4:96 to about 10:90 and wherein providing about 0.03 to about 0.08% (w/w) of the admixture to an aqueous colloid suspension stabilizes the aqueous colloid suspension by forming a stable hydrocolloid. Preferably the weight ratio of *konjac* mannan to xanthan gum is about 4:96 to about 6:94 and more preferably the weight ratio is 5:95. In certain other non-limiting embodiments of the present invention, the composition is provided as a premixed dry powder blend. In certain other non-limiting embodiments of the present invention, the aqueous colloid suspension is a dairy milk, a non-dairy milk drink, a flavored dairy milk drink, a flavored non-dairy milk drink, a coffee drink, a protein shake, a nutritional supplement, an infant formula, a meal replacement drink, or a weight loss drink. In certain other non-limiting embodiments of the present invention, the aqueous colloid suspension is an ice cream base, syrup, pudding, dressing, gravy, mayonnaise, ketchup, toothpaste, lotion, liquid soap, conditioner, shampoo, body wash, or sunscreen.

The present invention also provides a drink composition comprising an admixture of *konjac* mannan and xanthan gum, protein solids, and water wherein the admixture has a weight ratio of *konjac* mannan to xanthan gum that is about 4:96 to about 10:90, and the drink composition is stabilized with about 0.03 to about 0.08% (w/w) of the admixture. Preferably the admixture has a weight ratio of *konjac* mannan to xanthan gum that is about 4:96 to about 6:94 and more preferably the weight ratio is 5:95. Preferably the drink composition is stabilized with about 0.05 to about 0.07% (w/w) of the admixture and more preferably 0.06% (w/w) of the admixture.

In certain other non-limiting embodiments of the present invention, the drink composition further comprises a salt. Preferably the salt is sodium phosphate, calcium phosphate, magnesium phosphate, potassium phosphate, sodium citrate, or potassium citrate. Preferably the salt is provided in an amount from about 0.05% to about 0.20% (w/w). In certain other non-limiting embodiments of the present invention, the protein solid is wheat protein, egg protein, collagen protein, whey protein, casein protein, gluten, pea protein, soy protein, silk protein, or combinations thereof. In certain other non-limiting embodiments of the present invention, the concentration of protein solid is at least 1% of the drink, preferably about 2 to about 20% of the drink composition, more preferably about 2 to about 10% of the drink composition, and most preferably about 2 to about 4% of the drink composition. In certain other non-limiting embodiments of the present invention, the drink composition has a pH about 6.5 to about 7.8. In certain other non-limiting embodiments of the present invention, the stability of the drink composition is measured using flow disruption, marbling, flocculation, phase separation and sedimentation. In certain other non-limiting embodiments of the present invention, the drink composition remains stable when stored at a temperature about 4° C. to about 25° C. In certain other non-limiting embodiments of the present invention, the drink composition is a dairy milk, a non-dairy milk drink, a flavored dairy milk drink, a flavored non-dairy milk drink, a coffee drink, a protein shake, a nutritional supplement, an infant formula, a meal replacement drink, or a weight loss drink. In certain other non-limiting embodiments of the present invention, the drink composition further comprises another hydrocolloid, such as carrageenan, gellan, guar, alginate, starch, or a combination thereof to achieve desirable texture, mouth feel, and stability. In certain other non-limiting embodiments of the present invention, the drink composition further comprises a cellulose, such as carboxymethyl cellulose (CMC), microcrystalline cellulose (MCC), or a combination thereof.

The present invention provides a method for stabilizing an aqueous colloid suspension comprising adjusting the weight ratio of *konjac* mannan to xanthan gum in an admixture and providing an amount of the admixture to the aqueous colloid suspension wherein the weight ratio of *konjac* mannan to xanthan gum is about 4:96 to about 10:90, the amount of the admixture provided is about 0.03 to about 0.08% (w/w), and providing the admixture to the aqueous colloid suspension results in the formation of a stable hydrocolloid. In certain other non-limiting embodiments of the present invention, the aqueous colloid suspension is an ice cream base, syrup, pudding, dressing, gravy, mayonnaise, ketchup, toothpaste, lotion, liquid soap, conditioner, shampoo, body wash, or sunscreen.

The present invention also provides a method for stabilizing a drink composition comprising adjusting a weight ratio of *konjac* mannan to xanthan gum in an admixture and adding an amount of the admixture to the drink wherein the weight ratio is from about 4:96 to about 6:94, the amount is from about 0.03 to about 0.08% (w/w). In certain other non-limiting embodiments of the present invention, the drink composition is a dairy milk, a non-dairy milk drink, a flavored dairy milk drink, a flavored non-dairy milk drink, a coffee drink, a protein shake, a nutritional supplement, an infant formula, a meal replacement drink, or a weight loss drink.

BRIEF DESCRIPTION OF THE FIGURES

FIG. 1 is an exemplary picture of a chocolate milk sample that exhibits phase separation and marbling.

DETAILED DESCRIPTION OF THE INVENTION

The invention relates to an admixture of *konjac* mannan and xanthan gum combined in a specific weight ratio, stabilized aqueous colloid suspensions containing the admixture, stabilized drink composition containing the admixture, and methods for stabilizing aqueous colloid suspensions and drink compositions. It is to be understood that the term admixture is used for ease of reference and does not require that *konjac* mannan and xanthan gum must be provided only as a mixture or together at the same time. It is within the scope of the invention for *konjac* mannan and xanthan gum to be provided in the requisite amounts as a mixture, simultaneously as separate components, or sequentially as separate components. In the context of this invention the preferred form of *konjac* mannan and xanthan gum are ones that are food grade. Food grade versions of *konjac* mannan and xanthan gum can be commercially obtained from numerous suppliers. Commercially available food grade xanthan gum include Keltrol® (CP Kelco, Atlanta, Ga.), N.J.), Satiaxane® (Cargill, Minneapolis, Minn.), Grindsted® xanthan (Dupont Danisco, Tarrytown, N.Y.), and Ticaxan® (Tic Gums, White Marsh, Md.). Commercially available food grade *konjac* mannan includes Nutricol® XP 3464 (FMC BioPolymer, Philadelphia, Pa.).

The inventors have discovered that the combination of xanthan gum and *konjac* mannan in specific weight ratios has improved stabilizing function in aqueous colloid suspensions and drink compositions without causing flow disruptions. When added to the drink compositions that include water-insoluble solids (for example protein solids), water, and optionally a salt, there are significant improvements in stability even when added in very small amounts while maintaining creamy mouth feel and smooth flow characteristics. Compared to drink compositions without the admixture of konjac mannan and xanthan gum, drink compositions containing the admixture showed significantly improved stability when stored at either room temperature (about 25° C.) or refrigerated (about 4° C.). The improved stability was measured using in a number of different methods including measuring levels of marbling, flocculation, phase separation, and sedimentation.

It has been discovered that the synergistic interaction between xanthan gum and konjac mannan is also present for the claimed weight ratios of the konjac mannan to xanthan gum and advantageously allows for small usage amounts to effectively stabilize drink compositions. Furthermore, addition of the requisite amounts of konjac mannan and xanthan gum did not detrimentally affect the flow characteristics of the drink composition. The weight ratio of konjac mannan to xanthan gum allows for flow characteristics desired in drink applications without sacrificing stability improvements. The combination of xanthan gum and konjac mannan is also able to stabilize drink compositions containing proteins that are known to lower the viscosity of soluble fibers such as xanthan gum and konjac mannan. Furthermore the stability and texture of certain drink compositions containing the combination of xanthan gum and konjac mannan are improved with the addition of a salt. This is surprising given that at low concentrations of xanthan gum, increasing salt concentration decreases the viscosity of xanthan gum and therefore the stabilizing effects of xanthan gum.

The admixture of konjac mannan and xanthan gum, when provided in the specific weight ratio and amounts according to the present invention, stabilizes aqueous colloid suspensions and drink compositions by minimizing marbling, flocculation, phase separation and sedimentation during storage conditions between about 4° C. to about 25° C. without causing flow disruption when poured. The stabilized drink composition preferably contains more than about 1% water-insoluble solids, more preferably more than about 2% water-insoluble solids, and most preferably more than about 4% water-insoluble solids. Water-insoluble solids include but are not limited to protein solids, cocoa solids, fat solids, and minerals. Protein solids include but are not limited to wheat protein, egg protein, collagen protein, whey protein, casein protein, gluten, pea protein, soy protein, silk protein, or combinations thereof. Drink compositions include but are not limited to dairy milk, goat milk, sheep milk, buffalo milk, hemp milk, soy milk, almond milk, oat milk, hazelnut milk, rice milk, coconut milk, peanut milk, flavored milk, milk shakes, protein drinks, meal replacement drinks, and weight loss drinks. The drinks may be reconstituted from solid or from liquid concentrates.

The invention is further illustrated with reference to the following Examples.

EXAMPLE I

Characterizing Stability

Samples tested for stability were aseptically transferred into 250 ml Sterile PETG Nalgene® media bottles up to the 250 ml mark then stored either in a refrigerator (about 4° C.) or at room temperature (about 23° C.). For example ten (10) bottles were filled with each sample allowing for a bottle to be tested for each temperature and for each of the five time points over a period of 2 months (1 day, 1 week, 2 weeks, 4 weeks, and 8 weeks). Multiple of ten bottles may be used in order to perform the tests in duplicate (20 bottles) or triplicate (30 bottles). Phase separation was measured by the amount of top and/or bottom phase development over the course of 2 months (1 day, 1 week, 2 weeks, 4 weeks, 8 weeks) with a ruler in mm Sedimentation was scored by the level of sediment layers on a scale of 0-4 (0 is 0 mm, 1 is up to and including 2 mm, 2 is greater than 2 mm up to and including 4 mm, 3 is greater than 4 mm up to and including 6 mm, and 4 is greater than 6 mm), Flocculation was scored using a visual determination of the amount of coagulated particles present on the inside walls of the beverage container after pouring out the sample on a scale of 0-4 (0=no coagulation, 4=high coagulation). Marbling was measured using a visual determination of the amount of color separation or streaking present while the samples were at rest. Marbling is evaluated on a scale of 0-4 (0=no color separation, 4=high levels of color separation). FIG. 1 is an exemplary picture of a sample exhibiting marbling. As seen in FIG. 1, the sample exhibits color separation 1 that is readily visible as non-homogenous floating particles. Some of these particles tend to form in vertical lines called streaking 2. A small amount of top phase separation 3 is also visible. Flow characteristics were evaluated on a scale from 0 to 4 by visually inspecting the samples during pouring for gel formation and rippling. Rippling appears as discrete wave-like formations that intermittently disrupt flow and increase the level of turbulence. A score of 0 indicates the absence of rippling. A score of 1 indicates light rippling which all rippling disappears after the sample is poured one time. A score of 2 indicates moderate rippling which requires that the sample is poured twice before all rippling is removed. A score of 3 indicates strong rippling where rippling still appears after the sample is poured twice and is also indicated by a burping noise during the initial pouring. The presence of gelled pieces was scored as 4. Viscosity of the samples was measured using a Brookfield LV #1 at 60 rpm using 15 revolutions. The shear storage modulus (G') of the samples was also measured using a TA Instruments AR 1500 ex Rheometer with 40 mm Standard Steel Parallel Plate, a 250 um gap, and kept at 25° C.

EXAMPLE II

Chocolate Soy Milk Drink

Konjac mannan and xanthan gum admixtures were prepared using five different weight ratios ranging from 25:75 to 0:100, konjac mannan to xanthan gum. Each of the admixtures was added to the other dry components (sugar, cocoa, and salt) then blended together so that the final use concentration of the admixture is 0.06% (w/w). The blended dry components were then added to the mixture of soy base and water. The mixture was blended using a propeller mixer at medium shear for 30 minutes until the dry components were uniformly incorporated. The mixture was then processed using ultra high temperature processing using indirect steam injection. The processed mixture was then homogenized at 2000 psi/500 psi and cooled. For each of the different admixture weight ratios, a set of 250 ml Nalgene bottles was aseptically filled with the homogenized mixture made from each admixture. Half of the bottles from each set were stored in refrigerated conditions and the remaining half at room temperature. After one week each sample bottle was observed for marbling, flocculation, sedimentation, rippling, and gel formation. Phase separation for both top and bottom phase formation was measured. Flow characteristics were also observed during pouring. Finally the viscosity and storage modulus were measured.

TABLE 1

Chocolate Soy Milk Drink Stability at 1 Week

| Ratio (konjac:xanthan) | 15:85 | | 10:90 | | 5:95 | | 0:100 | |
|---|---|---|---|---|---|---|---|---|
| Soy Base + Water | 90.1225% | | 90.1225% | | 90.1225% | | 90.1225% | |
| Sugar + Cocoa + CaCO3 + Salt | 9.8175% | | 9.8175% | | 9.8175% | | 9.8175% | |
| Konjac Mannan | 0.0090% | | 0.0060% | | 0.0030% | | 0.0000% | |
| Xanthan Gum | 0.0510% | | 0.0540% | | 0.0570% | | 0.0600% | |
| Total | 100% | | 100% | | 100% | | 100% | |
| Storage temp ° C. | 23.9 | 4.4 | 23.9 | 4.4 | 23.9 | 4.4 | 23.9 | 4.4 |
| Viscosity (cps) | 42 | 62 | 34 | 54 | 32 | 50 | 25 | 41.5 |
| G' (osc. Stress - Pa) | 0.25 | | 0.13 | | 0.08 | | 0.06 | |
| Top Phase (mm) | 12 | 8 | 3 | 1 | 0 | 0 | 55 | 55 |
| Bottom phase (mm) | 0 | 0 | 0 | 0 | 0 | 0 | 0 | 0 |
| Marbling (0-4) | 0 | 0 | 0.5 | 0 | 0 | 0 | 0 | 0 |
| Flocculation (0-4) | 0 | 0 | 0 | 0 | 0 | 0 | 0 | 0 |
| Sedimentation (0-4) | 0 | 0 | 0 | 0 | 0 | 0 | 0 | 0 |
| Smooth | Yes | Yes | Yes | Yes | Yes | Yes | Yes | Yes |
| Rippled | No | No | No | No | No | No | No | No |
| Gel | No | No | No | No | No | No | No | No |

These results show that the weight ratio of *konjac* mannan to xanthan gum has a significant effect in level of stabilization achieved in chocolate soy milk drinks. When only xanthan gum is used there is an unacceptably high level of phase separation. However phase separation was also observed when too much *konjac* mannan was used. This shows that there is a narrow range for the weight ratio of *konjac* mannan to xanthan gum that is able to achieve the desired level of stabilization.

EXAMPLE III

Chocolate Dairy Milk

*Konjac* mannan and xanthan gum admixtures were prepared using two different weight ratios of *konjac* mannan to xanthan gum (10:90 and 5:95) and at two different usage concentrations (0.04% and 0.08%). Each of the admixtures was added to the other dry components (sugar, cocoa, and salt) then blended together. The blended dry components were then added dairy milk. The mixture was blended using a propeller mixer at medium shear for 30 minutes until the dry components were uniformly incorporated. The mixture was then processed using ultra high temperature processing using indirect steam injection. The processed mixture was then homogenized at 2000 psi/500 psi and cooled. For each of the different admixture weight ratio and usage concentration combinations, a set of 250 ml Nalgene bottles was aseptically filled with the homogenized mixture made from each admixture. Half of the bottles from each set were stored in refrigerated conditions and the remaining half at room temperature. After one week each sample bottle was observed for marbling, flocculation, sedimentation, rippling, and gel formation. Phase separation for both top and bottom phase formation was measured. Flow characteristics were also observed during pouring. Finally the viscosity and storage modulus were measured.

TABLE 2

Chocolate Dairy Milk Drink Stability at 1 Week

| Ratio (konjac:xanthan) | 10:90 | | 10:90 | | 5:95 | | 5:95 | |
|---|---|---|---|---|---|---|---|---|
| Milk - 1.0% Fat | 89.41% | | 89.41% | | 89.43% | | 89.41% | |
| Sugar | 5.95% | | 5.95% | | 5.95% | | 5.95% | |
| Cocoa | 1.25% | | 1.25% | | 1.25% | | 1.25% | |
| Konjac Mannan | 0.006% | | 0.008% | | 0.003% | | 0.004% | |
| Xanthan Gum | 0.054% | | 0.072% | | 0.057% | | 0.076% | |
| Total | 100% | | 100% | | 100% | | 100% | |
| Usage concentration | 0.06% | | 0.08% | | 0.06% | | 0.08% | |
| Storage temp ° C. | 23.9 | 4.4 | 23.9 | 4.4 | 23.9 | 4.4 | 23.9 | 4.4 |
| Viscosity (cps) | 34 | 52 | 57 | 86 | 26 | 38 | 39 | 58 |
| G' (osc. Stress - Pa) | — | | .441 | | .117 | | .230 | |
| Top Phase (mm) | 0 | 0 | 0 | 0 | 0 | 0 | 0 | 0 |
| Bottom phase (mm) | 0 | 0 | 0 | 0 | 0 | 0 | 0 | 0 |
| Marbling (0-4) | 0.5 | 0.5 | 0 | 0 | 0 | 3 | 0 | 0 |
| Flocculation (0-4) | 0 | 0 | 0 | 0 | 0 | 0 | 0 | 0 |
| Sedimentation (0-4) | 0 | 0 | 0 | 0 | 0 | 0 | 0 | 0 |
| Smooth | Yes | No | No | No | Yes | Yes | Yes | Yes |
| Rippled | No | Yes | Yes | Yes | No | No | No | No |
| Gel | No | No | No | No | No | No | No | No |

These results show that at lower weight ratios of *konjac* mannan to xanthan gum a wider range of usage concentrations can be used to stabilize chocolate dairy milk drinks without a risk of creating flow disruptions. At higher weight ratios there is also the risk of generating rippled textures which are undesirable for drink applications.

EXAMPLE III

Chocolate Dairy Milk with a Buffer Salt

Different amounts of a buffer salt were added to samples containing *konjac* mannan and xanthan gum in a 6:94 weight ratio of *konjac* mannan to xanthan gum and a usage concentration of 0.06%. Samples were otherwise prepared and tested as previously described. The addition of the buffering salt, disodium phosphate, improved stability and mouth feel of the drink compositions for both storage conditions. At these levels of *konjac* mannan, xanthan gum, and disodium phosphate, the viscosity of the samples increased in a dose dependent manner with the addition of disodium phosphate. This data shows that the addition of a buffering salt such as disodium phosphate, further improves the stability of drink compositions.

TABLE 3

Chocolate Dairy Milk Drink with a Buffering Salt Stability at 2 Weeks

| Disodium Phosphate | 0.00% | | 0.10% | | 0.15% | |
|---|---|---|---|---|---|---|
| Storage temp ° C. | 23.9 | 4.4 | 23.9 | 4.4 | 23.9 | 4.4 |
| Viscosity (cps) | 28 | 39 | 29 | 45 | 31 | 48 |
| Top Phase (mm) | 0 | 0 | 0 | 0 | 0 | 0 |
| Bottom phase (mm) | 5 | 6 | 0 | 0 | 0 | 0 |
| Marbling (0-4) | 1 | 1 | 0 | 0 | 0 | 3 |
| Flocculation (0-4) | 0 | 0 | 0 | 0 | 0 | 0 |
| Sedimentation (0-4) | 0 | 0 | 0 | 0 | 0 | 0 |
| Smooth | Yes | Yes | Yes | Yes | Yes | Yes |
| Rippled | No | No | No | No | No | No |
| Gel | No | No | No | No | No | No |

EXAMPLE IV

Additional of Buffering Salts

Various buffering salts were added to samples containing *konjac* mannan and xanthan gum in a 5:95 weight ratio of *konjac* mannan to xanthan gum and a usage concentration of 0.06%. These buffering salts were added at a concentration of 0.15% to test their ability to also improve the stability of drink compositions. Samples were otherwise prepared and tested as previously described. The buffering salts tested include: disodium phosphate (DSP), sodium chloride (NaCl), dipotassium phosphate (DKP), sodium citrate (Na-Citrate), and potassium citrate (K-Citrate). Each of these salts showed improved the stability and mouth feel of drink compositions in both storage conditions. This data shows that several different buffering salts are able to further improve the stability of drink compositions.

TABLE 4

Two Week Storage Stability of Samples Containing Various Buffering Salts

| Buffering Salt | DSP | | NaCl | | DKP | | Na-Citrate | | K-Citrate | |
|---|---|---|---|---|---|---|---|---|---|---|
| Storage temp ° C. | 23.9 | 4.4 | 23.9 | 4.4 | 23.9 | 4.4 | 23.9 | 4.4 | 23.9 | 4.4 |
| Viscosity (cps) | 31 | 46.5 | 27 | 38 | 30 | 46 | 30.5 | 50 | 29.5 | 46 |
| Top Phase (mm) | 0 | 0 | 0 | 0 | 0 | 0 | 0 | 0 | 0 | 0 |
| Bottom phase (mm) | 0 | 0 | 0 | 0 | 0 | 0 | 0 | 0 | 0 | 0 |
| Marbling (0-4) | 0.5 | 0.5 | 0.5 | 0.5 | 0 | 0.5 | 0 | 0 | 0 | 0 |
| Flocculation(0-4) | 0 | 0 | 0 | 0 | 0 | 0 | 0 | 0 | 0 | 0 |
| Sedimentation(0-4) | 0 | 0 | 0 | 0 | 0 | 0 | 0 | 0 | 0 | 0 |
| Smooth | Yes | Yes | Yes | Yes | Yes | Yes | Yes | Yes | Yes | Yes |
| Rippled | No | No | No | No | No | No | No | No | No | No |
| Gel | No | No | No | No | No | No | No | No | No | No |

While the present invention has been described with respect to a limited number of embodiments, those skilled in the art will appreciate that numerous modifications and variations of the present invention are possible in light of the above teaching without deviating from the true spirit and scope of the present invention.

What is claimed is:

1. A composition for making an aqueous hydrocolloid suspension comprising an admixture of konjac mannan and xanthan gum wherein the admixture is in a weight ratio of konjac mannan to xanthan gum that is about 4:96 to about 10:90 and wherein providing about 0.03 to about 0.08% (w/w) of the admixture to an aqueous colloid suspension stabilizes the aqueous colloid suspension.

2. The composition of claim 1, wherein the weight ratio of konjac mannan to xanthan gum is about 4:96 to about 6:94.

3. The composition of claim 1, wherein the weight ratio of konjac mannan to xanthan gum is 5:95.

4. The composition of claim 1, wherein the composition is provided as a premixed dry powder blend.

5. The composition of claim 1, wherein the aqueous hydrocolloid suspension is a dairy milk, a non-dairy milk drink, a flavored dairy milk drink, a flavored non-dairy milk drink, a coffee drink, a protein shake, a nutritional supplement, an infant formula, a meal replacement drink, a weight loss drink, ice cream base, syrup, pudding, dressing, gravy, mayonnaise, ketchup, toothpaste, lotion, liquid soap, conditioner, shampoo, body wash, or sunscreen.

6. A drink composition comprising the admixture of claim 1, protein solids, and water wherein the admixture is in a weight ratio of konjac mannan to xanthan gum that is about 4:96 to about 10:90 and the drink composition is stabilized using about 0.03 to about 0.08% (w/w) of the admixture.

7. The drink composition of claim 6, wherein the weight ratio of konjac mannan to xanthan gum is about 4:96 to about 6:94.

8. The drink composition of claim 6, wherein the drink composition is stabilized with about 0.05 to about 0.07% (w/w) of the admixture.

9. The drink composition of claim 6, further comprising a buffering salt.

10. The drink composition of claim 9, wherein the buffering salt is at least one of sodium phosphate, potassium phosphate, sodium citrate, or potassium citrate, and the buffering salt is provided in an amount from about 0.05% to about 0.20% (w/w).

11. The drink composition of claim 6, wherein the protein solid is wheat protein, egg protein, collagen protein, whey protein, casein protein, gluten, pea protein, soy protein, silk protein, nut protein, rice protein, or combinations thereof.

12. The drink composition of claim 6, wherein the concentration of protein solid is about 1% to about 4% of the drink composition.

13. The drink composition of claim 6, wherein the drink composition has a pH of about 6.5 to about 7.8.

14. The drink composition of claim 6, wherein the stability of the drink composition is measured using at least one of flow disruption, marbling, flocculation, phase separation and sedimentation.

15. The drink composition of claim 6, wherein the drink composition remains stable when stored for at least one day at a temperature of about 4° C. to about 25° C.

16. The drink composition of claim 6, wherein the drink composition is dairy milk, a non-dairy milk drink, a flavored dairy milk drink, a flavored non-dairy milk drink, a coffee drink, a protein shake, a nutritional supplement, an infant formula, a meal replacement drink, or a weight loss drink.

17. A method for stabilizing an aqueous hydrocolloid suspension comprising adding the admixture of claim 1 to the aqueous hydrocolloid suspension, the amount of the admixture provided is about 0.03 to about 0.08% (w/w).

18. The method of claim 17, wherein the aqueous colloid suspension is an ice cream base, syrup, pudding, dressing, gravy, mayonnaise, ketchup, toothpaste, lotion, liquid soap, conditioner, shampoo, body wash, or sunscreen.

19. The method of claim 17, wherein the aqueous hydrocolloid suspension is a drink composition.

20. The method of claim 19, wherein the drink composition is dairy milk, a non-dairy milk drink, a flavored dairy milk drink, or a flavored non-dairy milk drink, coffee drink, protein shake, a nutritional supplement, an infant formula, a meal replacement drink, or a weight loss drink.

* * * * *